United States Patent
Sovik et al.

(10) Patent No.: US 6,414,497 B1
(45) Date of Patent: *Jul. 2, 2002

(54) PAVING MATERIAL ANALYZER SYSTEM AND METHOD

(75) Inventors: Robert A. Sovik, Clifton Park; Richard N. Hosterman, Buskirk; George G. Moross, Scotia, all of NY (US)

(73) Assignee: TransTech Systems, Inc., Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/565,022

(22) Filed: May 4, 2000

(51) Int. Cl.[7] .............................................. G01R 27/26
(52) U.S. Cl. ...................... 324/663; 324/687; 324/690; 324/665; 324/675
(58) Field of Search ............................ 324/663, 687, 324/690, 665, 675

(56) References Cited

U.S. PATENT DOCUMENTS

| | | | |
|---|---|---|---|
| 3,400,331 A | 9/1968 | Harris | 324/671 |
| 3,671,857 A | 6/1972 | Bergmanis et al. | 324/663 |
| 3,694,742 A | 9/1972 | Bergmanis et al. | 324/663 |
| 3,781,672 A | 12/1973 | Maltby et al. | 324/663 |
| 3,784,905 A | 1/1974 | Blackwell | 324/663 |
| 3,882,381 A | 5/1975 | Gregory | 324/667 |
| 3,967,912 A | 7/1976 | Parker | 404/84.05 |
| 4,099,118 A | 7/1978 | Franklin et al. | 324/671 |
| 4,389,136 A | 6/1983 | Fehrenbach | 404/75 |
| 4,433,286 A | 2/1984 | Capots et al. | 324/663 |
| 4,468,610 A | 8/1984 | Hanson | 324/665 |
| 4,604,612 A | 8/1986 | Watkins et al. | 340/582 |
| 4,766,369 A | 8/1988 | Weinstein | 324/670 |
| 4,817,021 A | 3/1989 | Sowerby et al. | 702/137 |
| 4,933,853 A | 6/1990 | Musil et al. | 701/50 |
| 4,972,154 A | 11/1990 | Bechtel et al. | 324/663 |
| 5,051,026 A | 9/1991 | Sovik | 404/118 |
| 5,088,854 A | 2/1992 | Sovik | 404/72 |
| 5,134,380 A | 7/1992 | Jonas | 324/674 |
| 5,138,268 A | 8/1992 | Mulkey et al. | 324/671 |
| 5,210,500 A | 5/1993 | Pingel et al. | 324/667 |
| 5,213,442 A | 5/1993 | Sovik | 404/102 |
| 5,223,796 A | 6/1993 | Waldman et al. | 324/687 |
| 5,309,110 A | 5/1994 | O'Neill et al. | 324/674 |
| 5,363,051 A | 11/1994 | Jenstrom et al. | 324/661 |
| 5,378,994 A | 1/1995 | Novak et al. | 324/671 |
| 5,398,547 A | 3/1995 | Gerardi et al. | 73/170.26 |
| 5,436,565 A | 7/1995 | Gammell | 324/679 |
| 5,484,226 A | 1/1996 | Emerson et al. | 404/84.05 |
| 5,521,515 A | 5/1996 | Campbell | 324/674 |
| 5,551,288 A | 9/1996 | Geraldi et al. | 73/170.26 |
| 5,602,486 A | 2/1997 | Novak | 324/671 |
| 5,900,736 A | 5/1999 | Sovik et al. | 324/663 |

FOREIGN PATENT DOCUMENTS

FR    2593200    7/1987

OTHER PUBLICATIONS

Atkins, R. T., Pangburn, T., Bates, R. E., and Brockett, B. E., "Soil Moisture Determinations Using Capacitance Probe Methodology," U.S. Army Cold Regions Research and Engineering Laboratory, Special Report 98–2, Jan. 1998.

*Primary Examiner*—N. Le
*Assistant Examiner*—Wasseem H. Hamdan
(74) *Attorney, Agent, or Firm*—Hoffman, Warnick & D'Alessandro LLC; Spencer K. Warnick

(57) ABSTRACT

A paving material analyzer system is disclosed that uses paving material impedance to determine paving material density. The invention also includes a method for analyzing paving material, in particular, determining paving material density. The paving material density can also be used to determine a percentage of maximum compaction. A paving material analyzer is also disclosed that determines paving material density regardless of moisture presence on the paving material.

19 Claims, 4 Drawing Sheets

PAVING MATERIAL ANALYZER SYSTEM AND METHOD

BACKGROUND OF THE INVENTION

1. Technical Field

The present invention relates generally to paving material density analyzers. More particularly, the present invention relates to a paving material analyzer system and a method for analyzing paving material.

2. Related Art

During paving operations, paving material is usually laid at about 75% of acceptable compaction. Acceptable compaction is a recommended level of compaction that reduces variations in the material, such as air voids, that can create potential defects in the paving material. It is highly advantageous to compact the paving material to a level as close to acceptable compaction as possible. Unfortunately, the level of compaction is not readily apparent by viewing the compacted paving material. In order to address this problem, measurement of dielectric properties of paving material is known to be very useful for determining material density, a key indicator of compaction level.

One pavement density indicator device is that of Blackwell, U.S. Pat. No. 3,784,905. Blackwell's device measures dielectric properties of the asphalt, which is representative of the change in density in the asphalt. The device of Blackwell has many disadvantages. For example, in order to obtain a reading, the Blackwell device must be moved at extremely slow speeds across the material being tested and, accordingly, requires an extended time period to provide a determination. The Blackwell device, due to its excessive weight, also requires a large sled frame (contact area) to be dragged across the pavement surface. Another disadvantage is limited adjustability of the depth of measurement of the device caused by the given set of electrodes only being able to vary the depth of measurement by changing the height of the electrodes. Yet another disadvantage is the inability to measure density when the paving material is wet.

In another apparatus, a nuclear source is used to determine density of pavement material. This device has a variety of obvious drawbacks. For instance, the device requires a licensed operator and a radiation shield (e.g., a lead enclosure). Furthermore, the device is non-adjustable for area, time-consuming in use, and heavy.

Another disadvantage of the above-described devices is their inability to vary the shape and area of the sensing area. Altering the shape and area of the sensing area is advantageous for determining the density in particular pavement attributes, e.g., dips, joints, odd shaped patches, etc.

Yet another disadvantage of the above-described devices is that their operation speed is relatively slow. It is therefore desired to have a system which is faster than those available.

In view of the foregoing there is a long felt need for a reliable paving material analyzer system and method for analyzing paving material. There is also a need for a system and method that can correct for moisture on the paving material.

SUMMARY OF THE INVENTION

The invention overcomes the above shortcomings by providing in a first aspect of the invention, a paving material analyzer system comprising: a sensor; an electronic circuit operatively coupled to the sensor to generate an electrical field from the sensor proximate the paving material; and a data analyzer that determines a density of the paving material based on the effect of impedance characteristics of the paving material on the electrical field.

A second aspect of the invention provides a method for analyzing paving material comprising the steps of: determining an impedance of the paving material; and determining the density of the paving material based on the impedance determination of the paving material.

A third aspect of the invention provides a paving material analyzer system comprising: means for determining an impedance of the paving material; and means for determining the density of the paving material based on the impedance determination of the paving material.

In a fourth aspect of the invention is provided a paving material analyzer system comprising: a sensor; an electronic circuit operatively coupled to the sensor to generate an electrical field from the sensor proximate the paving material; and a density determining data analyzer that determines a density of the paving material regardless of moisture presence on the paving material.

The foregoing and other features and advantages of the invention will be apparent from the following more particular description of preferred embodiments of the invention.

BRIEF DESCRIPTION OF THE DRAWINGS

The preferred embodiments of this invention will be described in detail, with reference to the following figures, wherein like designations denote like elements, and wherein.

DESCRIPTION OF THE PREFERRED EMBODIMENTS

While the preferred embodiments will be described in conjunction with the paving environment, other applications of the invention will become apparent to those skilled in the art. The limited description is intended only for ease of explaining the construction and operation of the device. Accordingly, "paving material" should be interpreted broadly to include all varieties of asphalt, cement, concrete, soil, sand, stones, bituminous material and all other forms of in-place material.

Figure 1:
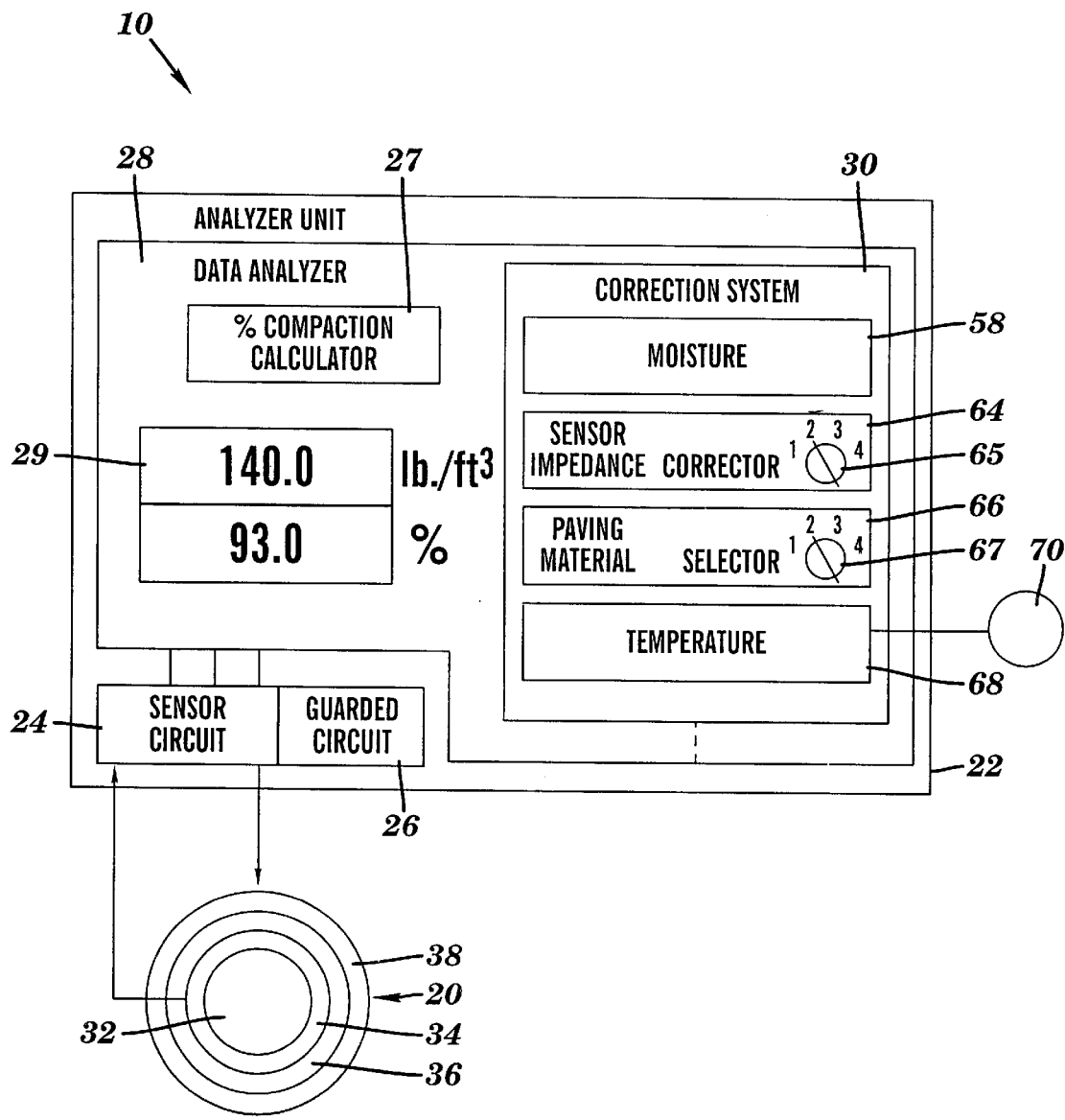
FIG. 1 shows a schematic view of a paving material analyzer system.

Referring to FIG. 1, a schematic view of a paving material analyzer system 10 is shown. System 10 includes a sensor 20 and an analyzer unit 22. Analyzer unit 22 preferably has a sensor circuit 24 and a data analyzer 28. Sensor circuit 24 is an electronic circuit that: 1) applies an electric potential to sensor 20 to generate, or transmit, an electrical field; and 2) receives the electrical field. Sensor circuit 24 preferably includes a guarded circuit 26. As will be described in greater detail below, data analyzer 28 may include a percentage compaction calculator 27, a display 29 and a correction system 30.

Figure 2:
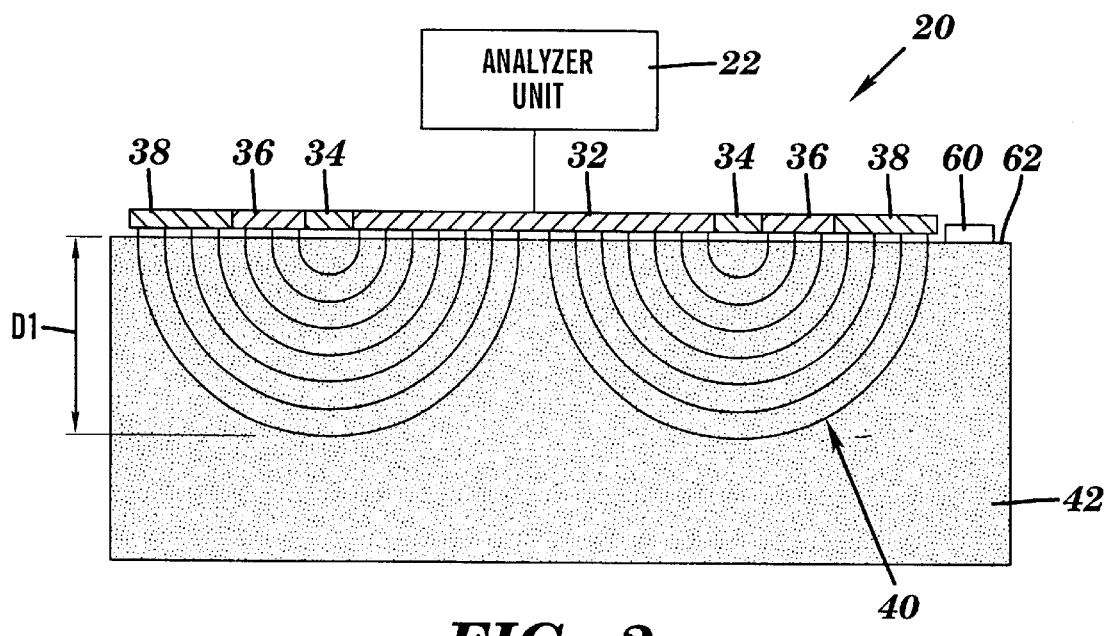
FIG. 2 shows a cross-sectional view of the system of FIG. 1 in use.

An exemplary structure of sensor 20 is shown in FIGS. 1 and 2. Sensor 20 preferably includes an active inner element 32 surrounded by an intermediate ground element 34 which is surrounded by a first outer element 36 and a second outer element 38. As shown in FIG. 2, an electrical field 40 is created proximate paving material 42 by applying an electric potential (from electronic circuit 24 shown in FIG. 1) through sensor 20. Electrical field 40 is transmitted from sensor 20 via element 38 and/or element 36 into adjacent paving material 42. Sensor 20 may be in contact with paving material 42 during use. Inner element 32 then receives this electrical field signal from paving material 42, the signal having been altered by the impedance characteristics of paving material 42. Each of elements 32, 34, 36, 38 may be constructed of any conducting material, but are preferably made of copper, aluminum or steel. Elements are held together and insulated from each other by a non-conductive material such as an epoxy.

Figure 3:
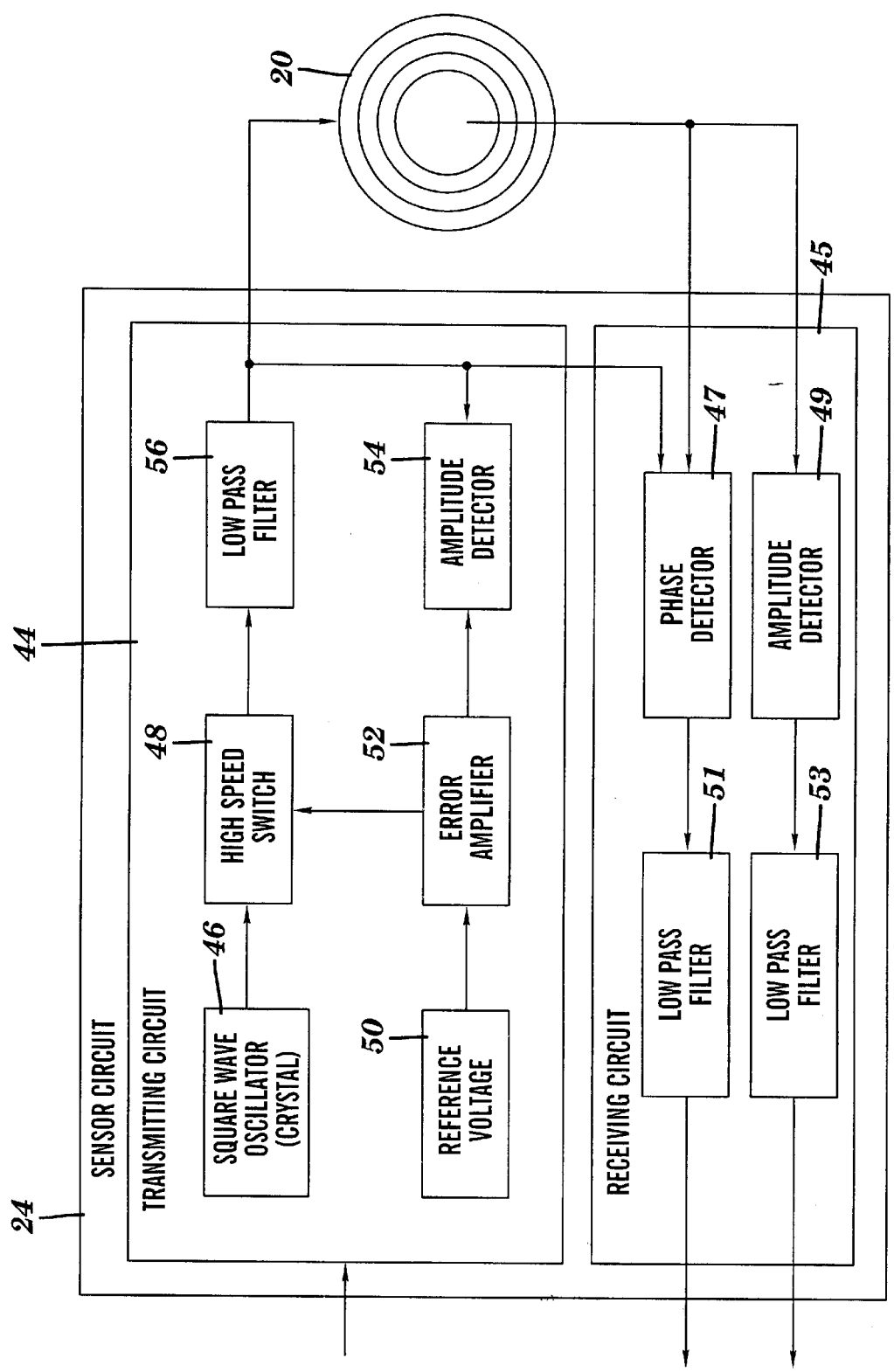
FIG. 3 shows a circuit diagram of a sensor circuit.

Turning to FIG. 3, sensor circuit 24 preferably includes a transmitting circuit 44 and a receiving circuit 45. While preferred embodiments of these circuits have been illustrated, it should be noted that these circuits 24, 44, 45 may take a variety of forms. The preferred embodiments disclosed for each should, therefore, not be taken as limiting the invention to any particular number or form of circuitry.

In the exemplary circuits shown in FIG. 3, transmitting circuit 44 is preferably a constant voltage source circuit. Circuit 44 includes a square wave oscillator (crystal) 46 coupled to a high speed switch 48. A reference voltage 50 is supplied to an error amplifier 52 that is also coupled to high speed switch 48. An amplitude detector 54 is also coupled to error amplifier 52. A low pass filter 56 is provided at an output of high speed switch 48. Output of low pass filter 56 is the constant voltage sine wave output for sensor 20. Amplitude detector 54 also receives the output of low pass filter 56 and maintains the constant voltage output. The output to sensor 20 preferably has a frequency in the range of 200 kHz to 15 MHz. It should be recognized that while a preferred constant voltage source circuit has been illustrated, other systems that provide a constant voltage source are also possible. Accordingly, the invention should not be limited to any particular form of constant voltage source circuitry.

In the exemplary receiving circuit 45, a phase detector 47 and an amplitude detector 49 receive the electrical field signal back from sensor 20. Phase detector 47 is also coupled to an amplitude detector 54, which it may share with transmitting circuit 44. Phase detector 47 and amplitude detector 49 feed to a low pass filter 51 and a low pass filter 53, respectively. The outputs of low pass filters 51, 53 are coupled to data analyzer 28 for analysis of the electrical field signal.

Returning to FIG. 1, regardless of the type of sensor circuit 24 used, it is preferred that a guarded circuit 26 is included so sensor circuit 24 and sensor 20 are guarded. In this setting, guarded circuit 26 would be coupled to an additional element 74, shown in FIG. 5. Element 74 acts as a guard element for sensor 20. It has been found that this promotes accuracy because determinations are not subject to stray fields.

As also shown in FIG. 1, system 10 includes a data analyzer 28. In a preferred embodiment, data analyzer 28 is a microcomputer configured to determine the density of paving material 42 based on the effect of the impedance characteristics of paving material 42 on electrical field 40. In particular, data analyzer 28 determines an impedance value of paving material 42, e.g., by comparing a transmitted electrical field signal versus a received electrical field signal that has passed through paving material 42. Data analyzer 28 uses the impedance value to determine a density value of paving material 42. Impedance has been found to be a more useful measure of density than predecessor systems' use of capacitance.

Data analyzer 28 is capable of determining paving material density in terms of: 1) variations in paving material density across a measurement area, and 2) actual density indications. In order to determine the density of paving material 42 in terms of variations in density, variations in impedance of electrical field 40 created by the impedance characteristics of paving material 42 are tracked.

In a preferred embodiment, however, data analyzer 28 is configured to mathematically provide actual density determinations, e.g., 140 lb/ft$^3$, and output them to a display 29. Density mathematical algorithms used to determine actual density indications may be created by modeling empirical data. Empirical data may be produced, for example, by calibrating a given sensor at a preferred operational setting with regard to specific types of paving material at known compaction densities. Mathematical modeling of the relationships between the measured impedance and known compaction densities results in a way to accurately determine density from an impedance of a specific type of paving material. Different mathematical algorithms can be created for different paving material and/or different sensors to make system 10 more accommodating, as will be described in more detail below. As one with skill in the art will appreciate, there may be other mechanisms other than mathematical modeling to determine actual density values. For instance, it may be possible to simply use the empirical data as a database to determine density, i.e., use the data as a lookup table.

Data analyzer 28 may also include a percentage compaction calculator 27 that calculates a percentage of maximum compaction, or percentage of air voids, of a particular paving material from the determination of density. The percentage can then be outputted to display 29. The relationship of density to a compaction percentage may be determined in many ways. One example method is by dividing the density determination by a known maximum compaction density for a particular paving material 42 that has been inputted to data analyzer 28. Data analyzer 28 3 may also be configured to calculate a compaction percentage without a separate calculator 27, i.e., as part of its operations discussed above.

As shown in FIG. 1, data analyzer 28 may also include a correction system 30. Correction system 30 may include a number of correction subsystems 58, 64, 66, etc. for making corrections to an impedance determination and, hence, determination of density and percentage compaction.

A first preferred correction subsystem 58 is a moisture corrector that corrects for moisture 60 on a top surface 62 of paving material 42, as shown in FIG. 2. In particular, it has been found that an increase in the phase angle of the measured impedance is indicative of increased moisture 60 on a top surface 62 of paving material 42. Similarly to the overall density mathematical algorithms discussed above, moisture correction mathematical algorithms can be created by modeling empirical data of moisture content. A moisture content mathematical algorithm can then be appropriately factored into the density mathematical algorithm to correct for moisture content, i.e., by removing a moisture content factor from the density mathematical algorithm. As a result, more accurate density determinations are possible. As with the density mathematical algorithms, a number of moisture content mathematical algorithms can be created for different paving material and/or different sensors to make system 10 more accommodating. With the above moisture corrector 58, a system 10 can determine the density of paving material based on the effect on the electrical field caused by the impedance characteristics of the paving material and regardless of moisture presence on the paving material.

Any impedance determination completed by system 10 automatically includes a quantity that is attributable solely to sensor 20, i.e., a sensor impedance. Accordingly, inaccuracies may result unless the sensor impedance is removed from the overall impedance determination. Sensor impedance may be created by a number of factors such as the type of a protective coating (not shown) that may be applied to sensor 20 and/or any air void that may be provided between a protective coating and sensor elements 32, 34, etc. Where a given system 10 will be used on only one paving material 42 and will not have a changeable sensor 20, a pre-set sensor impedance correction factor can be used to remove the pre-determined sensor impedance from the density mathematical algorithms. However, where system 10 may be used with different sensors 20, a sensor impedance corrector 64 is preferably provided as a second correction subsystem to remedy the problem. In this setting, a sensor impedance correction factor for each sensor may be predetermined, and a sensor selector 65 may be provided for choosing a given sensor and correction factor. Data analyzer 28 could then automatically correct for sensor impedance regardless of the sensor used. It should be recognized that other mechanisms for inputting a sensor impedance correction factor may be provided and not depart from the spirit of this invention. For instance, each sensor 20 may have a sensor impedance correction factor indicated thereon for input by a user into system 10. As an alternative, rather than simply providing a sensor impedance correction factor, sensor impedance corrector 64 may also operate to implement different density mathematical algorithms for each sensor that automatically account for sensor impedance.

Another correction subsystem 66 that may be provided is for selection of a particular paving material 42. For instance, if a particular paving material 42 is known to require special treatment by system 10, subsystem 66 could provide a paving material selector 67 so data analyzer 28 can automatically correct problems that may cause inaccuracies. In this setting, each common paving material would have a predetermined correction factor(s) associated therewith. Alternatively, paving material selector 67 may operate to implement different density mathematical algorithms for each paving material that automatically account for any necessary special treatment.

A temperature corrector 68 may also be provided as a correction subsystem. Temperature corrector 68 would include a thermometer 70 and would create a correction factor by way of a correction algorithm. For instance, it has been found that an increase in paving material temperature results in a higher density determination and that the density determination can be corrected by subtracting a density value proportional to paving material temperature.

Figure 4:
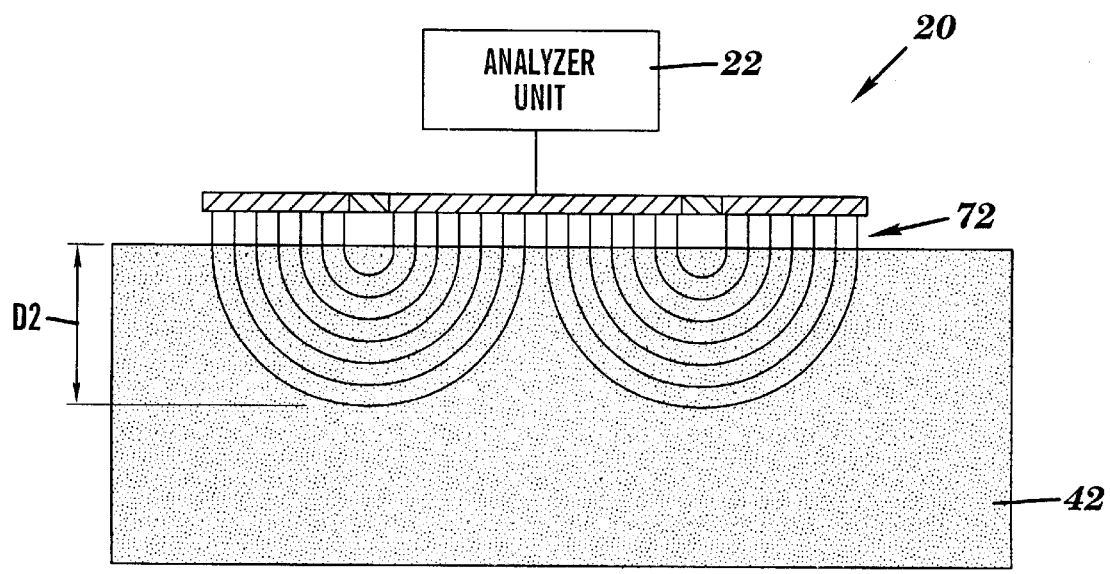
FIG. 4 shows a cross-sectional view of an alternative operational setting of the system of FIG. 1.

Other correction subsystems may be provided as will be recognized by one with skill in the art. For instance, as shown in FIG. 4, it is contemplated that sensor 20 can operate at a standoff distance from paving material 42. Capacitance caused by gap 72 between sensor 20 and paving material 42 can adversely affect the impedance determination if not corrected. To remedy this problem, an additional standoff distance corrector could be added that uses, for example, an RC oscillator system similar to that discussed in U.S. Pat. No. 5,900,736, which is hereby incorporated by reference.

It is understood that analyzer unit 22 and its components can be realized in hardware, software, or a combination of hardware and software. Furthermore, analyzer unit 22 may be realized in a centralized fashion in one computer system, or in a distributed fashion where different elements are spread across several interconnected computer systems, e.g., data analyzer 28 can split into an impedance determining unit, a density determining unit, etc. Any kind of computer system—or other apparatus adapted for carrying out the methods described herein—is suited. A typical combination of hardware and software could be a general purpose computer system with a computer program that, when being loaded and executed, controls data analyzer 28 such that it carries out the methods described herein. The present invention can also be embedded in a computer program product, which comprises all the features enabling the implementation of the methods described herein, and which—when loaded in a computer system—is able to carry out these methods. Computer program, software program, or planning software, in the present context mean any expression, in any language, code or notation, of a set of instructions intended to cause a system having an information processing capability to perform a particular function either directly or after either or both of the following: (a) conversion to another language, code or notation; (b) reproduction in a different material form.

Figure 6:
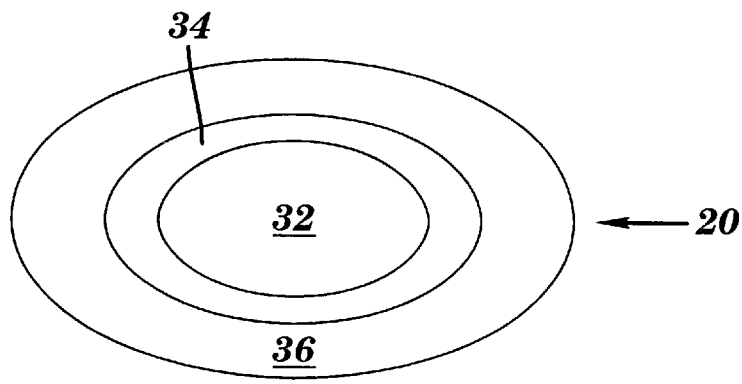
FIG. 6 shows a detail view of a second alternative embodiment of a sensor.
Figure 7:
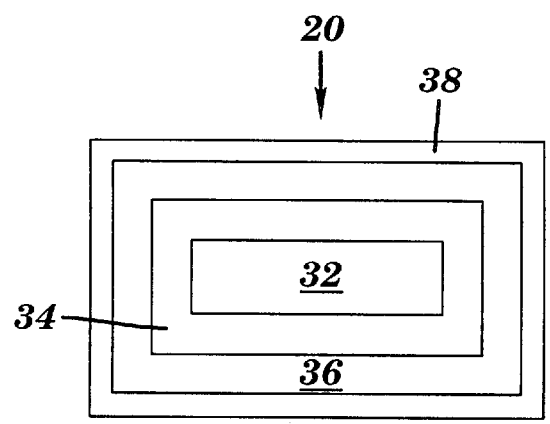
FIG. 7 shows a detail view of a third alternative embodiment of a sensor.
Figure 5:
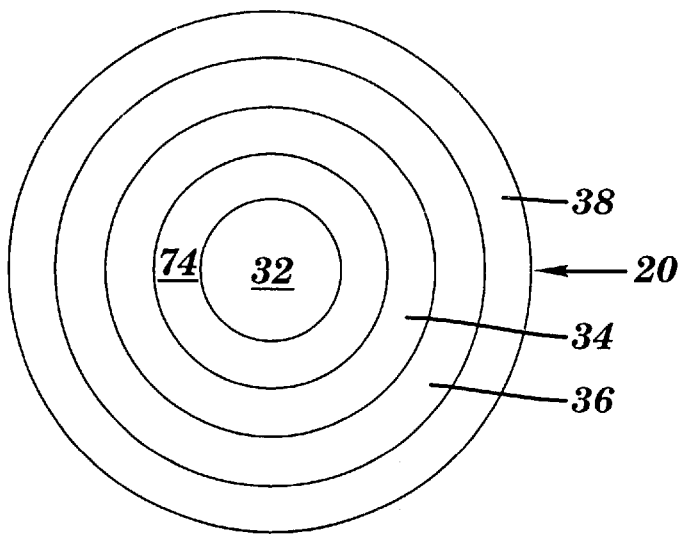
FIG. 5 shows a detail view of a first alternative embodiment of a sensor.

Referring to FIGS. 5–7, a variety of sensors 20 having different numbers of elements are shown. For instance, a sensor 20 shown in FIG. 5 has an additional guard element 74, and a sensor 20 shown in FIG. 6 has outermost element 38 removed. When guard element 74 is provided, it is coupled to guard circuit 26 so that sensor circuit 24 and sensor 20 are guarded. Additional elements surrounding those described above, and structured in similar fashion as those above, may be used to make system 10 more stable. Additional elements are advantageous to make the electrical field more uniform or compensate for other parameters that may interfere with impedance measurement, e.g., known electromagnetic interference.

FIGS. 5–7 also illustrate how the shape and size of sensors can be selectively different. The examples shown are a circular shape in FIG. 5; an elliptical shape in FIG. 6; and a polygonal, i.e., rectangular, shape in FIG. 7. Adjustability of the shape and size of sensor 20 is advantageous to system 10 because the shape and size of sensor 20, inter alia, dictates the depth of penetration and area of electrical field 40 and, accordingly, the volume of the field of test. For instance, as illustrated in FIG. 4, operation of a smaller sized sensor 20 allows the depth of penetration to be reduced to D2 as opposed to the depth D1 shown in FIG. 2. Being able to accurately control the depth of penetration prevents imprecise determinations when the signal penetrates through a new lift coat into an underlying surface that may not have the same density.

Changing the shape and size of sensor 20 also allows for a variation of the shape of the area tested. For instance, when a user wishes to determine density at a joint between two new lift coats, he can now use, for example, a long rectangular sensor as shown in FIG. 7 to assure accurate sensing along the joint.

Although FIGS. 5–7 show sensors in three preferred shapes, sensor 20 may take a variety of alternative shapes.

Furthermore, although the embodiments shown are fixed in nature, it is also envisioned to provide a sensor with an adjustable shape.

The provision of a constant voltage source circuit enables system 10 to detect material density with more accuracy and reliability than related art devices or the constant current source disclosed in U.S. Pat. No. 5,900,736. Constant voltage source circuit in sensor circuit 24 also provides a lower impedance sensor, which provides a stable system that is not alterable by environmental factors, e.g., electromagnetic interference. Accordingly, the potential for mismeasurement is reduced. Furthermore, system 10 is lightweight and allows for instantaneous and continuous determinations that reduces paving time. The provision of correction system 30 and its related subsystems makes system 10 even more accurate.

The invention also includes a method for analyzing paving material using the above-described system(s). The method includes the steps of determining an impedance of the paving material; and determining the density of the paving material based on the impedance determination of the paving material. The step of determining an impedance may include: providing a sensor; applying an electric potential through the sensor to generate an electrical field proximate the paving material; receiving the electrical field from the paving material; and determining an impedance of the paving material based on the effect of impedance characteristics of the paving material on the electrical field.

The step of determining an impedance may also include correcting the determination for an impedance of the sensor, and correcting the determination for moisture on a top surface of the paving material. The correction for moisture is preferably provided by monitoring a phase angle of the impedance to determine moisture on a top surface of the paving material, and correcting the impedance determination accordingly. An alternative step would be to calculate a percentage of full compaction of the paving material.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

We claim:

1. A paving material analyzer system comprising:
    a sensor;
    an electronic circuit operatively coupled to the sensor to generate an electrical field from the sensor proximate the paving material; and
    a data analyzer, operatively coupled to the electronic circuit, that determines a density of the paving material based on the effect of impedance characteristics of the paving material on the electrical field.

2. The system of claim 1, wherein the data analyzer corrects the density indication for an impedance of the sensor.

3. The system of claim 1, wherein the data analyzer includes a moisture corrector that corrects for moisture on a top surface of the paving material.

4. The system of claim 3, wherein the moisture corrector determines a moisture correction factor from a phase angle of the impedance of the paving material.

5. The system of claim 1, wherein the data analyzer includes a standoff distance corrector that corrects the density indication for a distance of the sensor to the paving material.

6. The system of claim 1, wherein the data analyzer includes a temperature corrector that corrects the density for temperature of the paving material.

7. The system of claim 1, wherein the electronic circuit operates at a frequency in the range of 200 kHz to 15 MHz.

8. The system of claim 1, wherein the electronic circuit and sensor are guarded.

9. The system of claim 1, wherein the sensor has a shape selected from the group consisting of circular, elliptical, and polygonal.

10. The system of claim 1, wherein the sensor is in contact with the paving material during use.

11. The system of claim 1, wherein the data analyzer includes a percentage compaction calculator.

12. A method for analyzing paving material comprising the steps of:
    determining an impedance of the paving material; and
    determining the density of the paving material based on the impedance determination of the paving material.

13. The method of claim 12, wherein the step of determining an impedance includes:
    providing a sensor;
    applying an electric potential to the sensor to generate an electrical field proximate the paving material; receiving the electrical field from the paving material; and
    determining an impedance of the paving material based on the effect of impedance characteristics of the paving material on the electrical field.

14. The method of claim 12, wherein the step of determining an impedance includes correcting the determination for an impedance of the sensor.

15. The method of claim 12, wherein the step of determining an impedance includes correcting the determination for moisture on a top surface of the paving material.

16. The method of claim 15, wherein the step of correcting includes monitoring a phase angle of the impedance to determine moisture on a top surface of the paving material.

17. The method of claim 12, further comprising the step of calculating a percentage of full compaction of the paving material.

18. A paving material analyzer system comprising:
    means for determining an impedance of the paving material; and
    means for determining the density of the paving material based on the impedance determination of the paving material.

19. A paving material analyzer system comprising:
    a sensor;
    an electronic circuit operatively coupled to the sensor to generate an electrical field from the sensor proximate the paving material; and
    a density determining data analyzer, operatively coupled to the electronic circuit, that determines a density of the paving material regardless of moisture presence on the paving material.

* * * * *